(12) United States Patent
Oberholtzer et al.

(10) Patent No.: US 6,448,453 B1
(45) Date of Patent: Sep. 10, 2002

(54) METHOD FOR THE PREPARATION OF CUMYLPHENOL

(75) Inventors: Jake Oberholtzer, Evansville, IN (US); Pramod Kumbhar, Bangalore (IN); Dave Sharber, Mt. Vernon, IN (US); Mannish V. Badani, Bangalore (IN)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/683,786

(22) Filed: Feb. 14, 2002

Related U.S. Application Data

(60) Provisional application No. 60/291,391, filed on May 16, 2001.

(51) Int. Cl.⁷ .............................................. C07C 39/12
(52) U.S. Cl. ....................................................... 568/744
(58) Field of Search .......................................... 568/744

(56) References Cited

U.S. PATENT DOCUMENTS

| | | | | |
|---|---|---|---|---|
| 2,882,322 A | * | 4/1959 | Griffin | |
| 4,906,791 A | | 3/1990 | Imanari et al. | 568/744 |
| 5,091,058 A | | 2/1992 | Davie | 203/33 |
| 5,185,475 A | | 2/1993 | Kissinger | 568/748 |
| 5,304,689 A | | 4/1994 | Kissinger | 568/748 |

* cited by examiner

*Primary Examiner*—Michael L. Shippen

(57) ABSTRACT

A method of preparing cumylphenol comprises reacting phenol and alpha-methylstyrene in the presence of an acid catalyst and an alkylbenzene. The method provides an inexpensive, selective process to cumylphenol.

22 Claims, 1 Drawing Sheet

METHOD FOR THE PREPARATION OF CUMYLPHENOL

CROSS REFERENCE TO RELATED APPLICATIONS

This application claims the benefit of the filing date of U.S. Provisional Application Serial No. 60/291,391, filed on May 16, 2001, which is hereby incorporated by reference.

BACKGROUND OF INVENTION

This disclosure relates to the synthesis of cumylphenols and particularly to the synthesis of p-cumylphenol.

The preparation of cumylphenols, and in particular the preparation of para-cumylphenol via the reaction of phenol with alpha-methylstyrene in the presence of a catalyst is well known in the art. See generally, U.S. Pat. No. 5,1 85,475 to Kissinger, U.S. Pat. No. 5,091,058 to Davie, and U.S. Pat. No. 4,906,791 to Imanari et al. While selective to some extent, a number of byproducts are nonetheless produced, including ortho-cumyl phenol, which must be subsequently separated. Furthermore, many of these processes require use of purified alpha-methylstyrene as a starting material. Commercially available alph-amethylstyrene originates as a by-product of the phenol production process, and thus contains numerous other components such as alkylbenzenes, predominantly cumene. The alpha-methylstyrene is isolated by distillation or other costly means. The cost of the purified alpha-methylstyrene adds to the cost of producing cumylphenols. There accordingly remains a need in the art for selective, economical processes to produce cumylphenol, and especially para-cumylphenol.

SUMMARY OF INVENTION

The above-described and other drawbacks and disadvantages of the prior art are alleviated by a method of preparing cumylphenol comprising reacting phenol and alpha-methylstyrene in the presence of an acid catalyst and an alkylbenzene to form a mixture comprising cumylphenol, wherein the alkylbenzene is present at about 1 weight percent (wt%) to about 90 weight percent based on the total weight of the reaction mixture.

DETAILED DESCRIPTION

Figure 1:
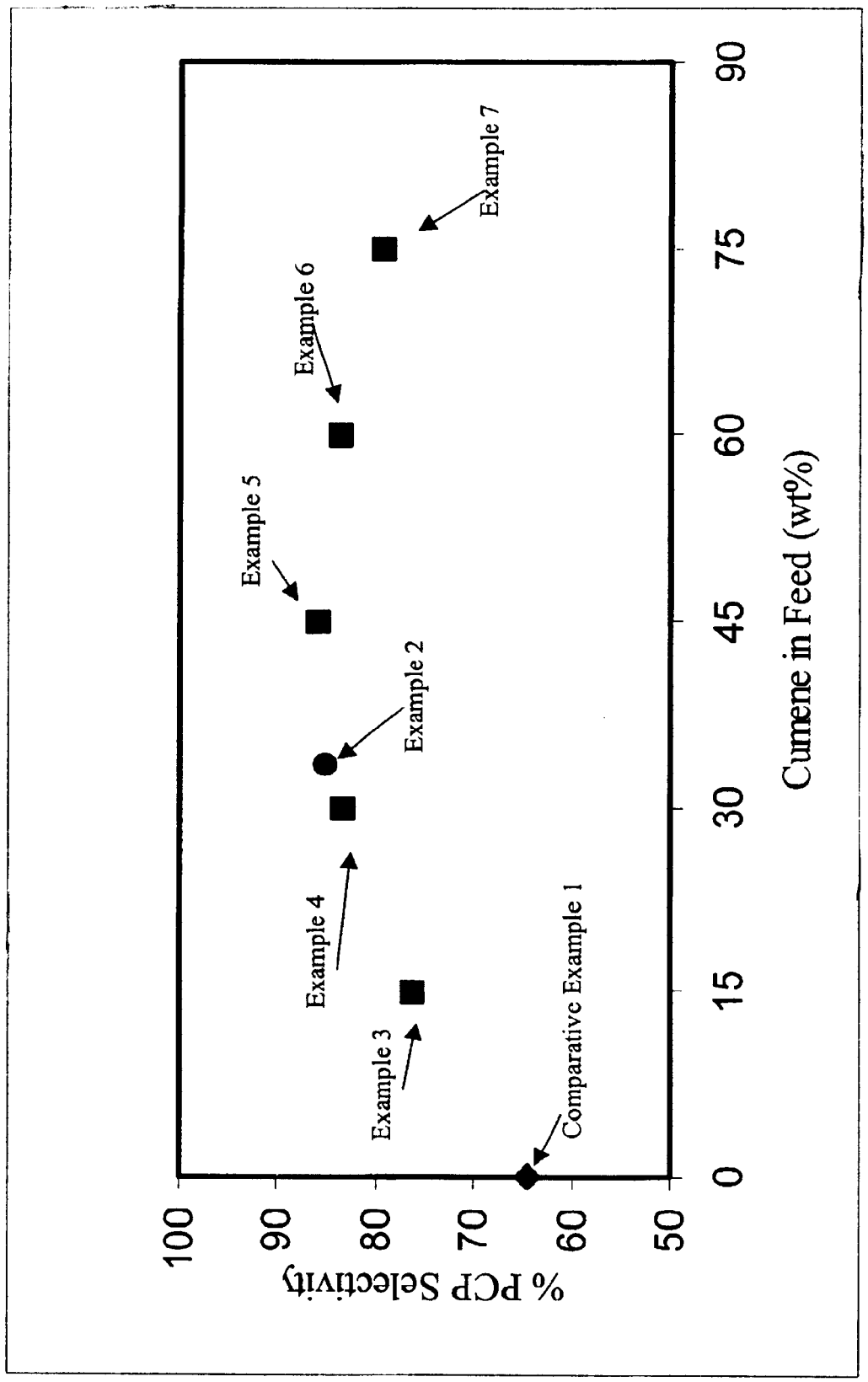
FIG. 1 is a graph showing reaction selectivity for para-cumylphenol versus weight percent of cumene in the total feed.

A method of preparing cumylphenol, particularly p-cumylphenol, comprises reacting phenol and alpha-methylstyrene in the presence of an acid catalyst and an alkylbenzene, preferably cumene, to form a mixture comprising cumylphenol, wherein the alkylbenzene is present at about 1 weight percent to about 90 weight percent based on the weight of the total reaction mixture. It has been unexpectedly found that the presence of an alkylbenzene in the production of cumylphenol increases the selectivity of the reaction to favor the formation of cumylphenol, particularly para-cumylphenol.

Phenol, alpha-methylstyrene (AMS), and a suitable alkylbenzene can be individually obtained from market sources. However, phenol and by-product alpha-methylstyrene are also readily available from the production of phenol from cumene, either separately or in the form of a mixture. Where alpha-methylstyrene is produced separately as a by-product from phenol production, it also generally contains an alkylbenzene such as cumene, in amounts of about 5 weight percent to about 90 weight percent of alkylbenzene based the total weight of alpha-methylstyrene and alkylbenzene. In a preferred embodiment, the alpha-methylstyreneby-product stream from the phenol production process is used directly to produce cumylphenols, without intermediate purification. This allows significant cost savings because there is no need to purify the alpha-methylstyrene (by distillation, e.g.,) prior to use.

Suitable alkyl benzenes comprise a phenyl ring having from one to five saturated alkyl substituents, wherein the alkyl substituents have 1 to about 12 carbon atoms. A preferred alkylbenzene is cumene. The amount of alkylbenzene present in the reaction is about 1% to about 90%, preferably about 20% to about 65%, and most preferably about 35% to about 55% weight percent, based on the total weight of the reaction mixture .

In the production of cumylphenol, the phenol is advantageously present in excess relative to the alpha-methylstyrene. A suitable excess may be readily determined by one of ordinary skill in the art, depending on reactivity of the starting materials and catalyst and reaction conditions, e.g., temperature, time of contact, and the like. A suitable excess generally is about 2 to about 15 molar equivalents of phenol to one molar equivalent of alpha-methylstyrene. A preferred excess is about 3 to about 13, and a more preferred excess is about 5 to about 11.5 molar equivalents of phenol relative to one molar equivalent of alpha-methylstyrene.

Suitable acid catalysts are known in the art. A solid acid catalyst is preferred to avoid unnecessary separation steps or acid recovery steps; however, homogeneous catalyst such as sulfuric acid, methane sulfonic acid and p-toluene sulfonic acid (PTSA) can be employed. Examples of solid acid catalyst include cation exchange resins, acid zeolites and acid aluminas. Exemplary solid acid catalyst systems are acidic cation exchange resins, which are generally well known, as are methods of their preparation. Strong acid ion exchange resins, such as those resins or polymers having a plurality of pendant sulfonic acid groups are preferred. Examples include sulfonated polystyrene or poly (styrenedivinylbenzene) copolymer and sulfonated phenol-formaldehyde resins. Such sulfonated resins are commercially available in water-swollen form as gellular and macroreticular types. Specific examples of commercially available resins are Amberlite® IR-120H, Amberlyst® 15, Amberlyst® 31, Dowex® 50-X-4, Dowex® MSC-IH, and Duolite® c-291. Further examples of such ion exchange resins, as well as methods for preparing such ion exchangers, are described in U.S. Pat. No. 3,037,052.

The exchange capacity of the acidic resin is preferably at least 2.0 milliequivalents of protons per gram (meq $H^+$/g) of dry resin, with exchange capacities in the range of from about 3.0 to about 5.5 meq $H^+$/g of dry resin particularly preferred. One preferred catalyst is the Amberlyst® types, which comprise styrene cross-linked with a monomer such as divinylbenzene or the like, and having pendant sulfonic acid groups attached to the aromatic nucleus of the styrene moiety.

Reaction conditions are readily determined by one of ordinary skill in the art, depending on factors such as type of starting material, length of contact, activity of the catalyst, amount of catalyst, and the like. The reaction is typically operated at inlet temperatures of about 40 to about 100° C., preferably about 45 to about 90° C., and more preferably about 50 to about 70° C. Reaction pressure is typically about 0.1 to about 0.7 MegaPascal (MPa) (about 14.7 pounds per square inch (psia) to about 100 psia).

The method may be operated continuously or batch-wise. The feed rate in the continuous method, as measured in weighted hourly space velocity (whsv), can vary from about 0.1 to about 12.0, preferably about 0.2 to about 6.0 pounds feed per hour per pound of dry catalyst. It is hypothesized that the production rate is dependent upon the viscosity of the reaction mass and that the presence of an alkylbenzene, especially cumene, in the feed stream of the reactor decreases the viscosity of the feed stream, lowering the pressure drop across the reactor and allowing for the reaction to be run at higher throughputs than reactions not containing an alkylbenzene.

After reaction, the reaction mixture may contain unreacted phenol, alpha-methylstyrene, alkylbenzene such as cumene, para-cumylphenol (PCP), ortho-cumylphenol (OCP), and by-products such as dicumylphenol, dimers of alpha-methylstyrene such as trimethylphenylindane (TMPI), and other components. Isolation of the desired cumylphenol may be performed by methods well known in the art to purify cumylphenols, such as distillation.

A preferred method of isolation comprises passing the reaction mixture through an anionic bed to remove any acid catalyst that may be present. The reaction mixture is then passed through a first distillation column operating under reduced pressure to remove any cumene and phenol that is present. The cumene and phenol may be recycled. The reaction mixture is then carried to a second distillation column operating under reduced pressure, generally about 20–40 mm Hga and an elevated temperature, typically about 170–225° C. wherein o-cumylphenol and TMPI are removed. The reaction mixture then proceeds to a third distillation column operating under reduced pressure, typically about 20–40 mm Hga and an elevated temperature, typically about 210–225° C. wherein the p-cumylphenol is separated from dicumylphenol.

The invention is further illustrated by the following non-limiting examples. All patents cited herein are incorporated by reference.

EXAMPLES

Batch reaction experiments were conducted to evaluate the effect of cumene concentration on reaction selectivity for PCP. Phenol, cumene and crude alpha-methylstyrene were obtained from a commercial cumene to phenol facility. Pure alpha-methylstyrene >99% was obtained from Aldrich. Amberlyst® 15 was obtained from Rohm & Hass. Determination of PCP and OCP concentration in the reaction mixture was carried out on a Hewlett Packard model 5890 Gas Chromatograph using a capillary column and a flame ionization detector.

Comparative Example 1

Phenol and approximately 10 weight percent of pure alpha-methylstyrene (>99%), based upon the total weight of the reaction mixture, were charged to a reaction based on the total weight of the reaction mixture, was added to the heated reaction medium. The reaction was allowed to run 4 hours and samples of the reaction were taken for analysis by gas chromatography. As shown in FIG. 1, the reaction demonstrates 64.4% selectivity.

Example 2

Example 2 was run according to the method of Comparative Example 1, with the substitution of crude alpha-methylstyrene for the pure alpha-methylstyrene. The crude alpha-methylstyrene was obtained from a phenol production plant. The crude alpha-methylstyrene contained about 20 weight percent of alpha-methylstyrene and about 78 weight percent of cumene based upon the total weight of the crude mixture. Using crude alpha-methylstyrene, the selectivity of the reaction for p-cumyl phenol was 85.1%.

Examples 3–7

Examples 3–7 were run according to the method of Comparative Example 1, with the substitution of a synthetic mixture of cumene and alpha-methylstyrene for the pure alpha-methylstyrene. The cumene was present at 15, 30, 45, 60, and 75 weight percent based on the weight of the total reaction mixture. Results are shown in FIG. 1.

As shown in the FIG. 1, the selectivity for the desired PCP is a function of the weight percent of cumene in the reaction feed. A surprising result was that an improved selectivity of the reaction was observed with cumene addition as compared with the reaction without cumene. An optimum selectivity resulted at the intermediate concentration of cumene and phenol. This improved selectivity is in addition to the benefit obtained from not having to purify the alpha-methylstyrene before utilizing it to produce cumylphenols, thus saving capital and operating costs. Additionally cumene reduces the viscosity of the reaction mixture enabling higher throughputs in fixed bed reactors.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method of preparing cumylphenol, comprising:
   reacting phenol and alpha-methylstyrene in the presence of an acid catalyst and about 1 to about 90 weight percent of an alkylbenzene based on the total weight of phenol, alpha-methylstyrene, acid catalyst and alkylbenzene, to form a product mixture comprising cumylphenol.

2. The method of claim 1, wherein the alkylbenzene is cumene.

3. The method of claim 2, wherein the cumene is present in an amount of about 20 to about 65 weight percent based upon the total weight of phenol, alpha-methylstyrene, acid catalyst and alkylbenzene.

4. The method of claim 2, wherein the cumene is present in an amount from about 35 to about 55 weight percent based upon the total weight of phenol, alpha-methylstyrene, acid catalyst and alkylbenzene.

5. The method of claim 2, further comprising isolating the cumylphenol from the product mixture.

6. The method of claim 1, wherein the alpha-methylstyrene is obtained as a by-product stream of a phenol production process.

7. The method of claim 6, wherein the by-product stream contains cumene.

8. The method of claim 2, wherein the method is operated at an inlet temperature of about 40 to about 100° C.

9. The method of claim 1, wherein the catalyst is an acidic ion exchange resin.

10. The method of claim 1, wherein the method is operated continuously.

11. The method of claim 1, wherein the method is operated batch-wise.

12. A method of preparing para-cumylphenol, comprising:

reacting an excess of phenol and alpha-methylstyrene in the presence of a solid acidic catalyst and about 1 to about 90 weight percent of an alkylbenzene based on the total weight of phenol, alpha-methylstyrene, acid catalyst and alkylbenzene to form a product mixture comprising para-cumylphenol.

13. The method of claim 12, wherein the alkylbenzene is cumene.

14. The method of claim 13, wherein the cumene is present in an amount of about 20 to about 65 weight percent based on the total weight of phenol, alpha-methylstyrene, acid catalyst and alkylbenzene.

15. The method of claim 13, wherein the cumene is present in an amount of about 35 to about 55 weight percent based on the total weight of phenol, alpha-methylstyrene, acid catalyst and alkylbenzene.

16. The method of claim 13, further comprising isolating the para-cumylphenol from the product mixture.

17. The method of claim 12, wherein the alpha-methylstyrene is obtained as a by-product stream of a phenol production process.

18. The method of claim 17, wherein the by-product stream contains cumene.

19. The method of claim 13, wherein the method is operated at an inlet temperature of about 50 to about 90° C.

20. The method of claim 12, wherein the catalyst is an acidic ion exchange resin.

21. The method of claim 12, wherein the method is operated continuously.

22. The method of claim 12, wherein the method is operated batch-wise.

* * * * *